United States Patent
Tapia et al.

(10) Patent No.: US 9,334,066 B2
(45) Date of Patent: May 10, 2016

(54) APPARATUS FOR AUTOMATED RASTERING OF AN END EFFECTOR OVER AN AIRFOIL-SHAPED BODY

(71) Applicant: The Boeing Company, Chicago, IL (US)

(72) Inventors: William Joseph Tapia, Kapowsin, WA (US); Michael D. Fogarty, Auburn, WA (US); Joseph L. Hafenrichter, Seattle, WA (US); Gary E. Georgeson, Tacoma, WA (US)

(73) Assignee: The Boeing Company, Chicago, IL (US)

( * ) Notice: Subject to any disclaimer, the term of this patent is extended or adjusted under 35 U.S.C. 154(b) by 389 days.

(21) Appl. No.: 13/861,934

(22) Filed: Apr. 12, 2013

(65) Prior Publication Data

US 2014/0305217 A1 Oct. 16, 2014

(51) Int. Cl.
*B64F 5/00* (2006.01)
*G01N 29/04* (2006.01)
*G01N 29/265* (2006.01)
*G01N 27/90* (2006.01)
*G01N 29/22* (2006.01)

(52) U.S. Cl.
CPC .......... *B64F 5/0045* (2013.01); *G01N 27/9013* (2013.01); *G01N 29/04* (2013.01); *G01N 29/225* (2013.01); *G01N 29/265* (2013.01); *G01N 2291/0289* (2013.01); *G01N 2291/044* (2013.01); *G01N 2291/102* (2013.01); *G01N 2291/2694* (2013.01); *Y10S 901/44* (2013.01)

(58) Field of Classification Search
CPC .............. G01N 29/225; G01N 29/265; G01N 2291/0289; G01N 2291/2638; G10K 11/004; B64F 5/0045

USPC ....................... 73/618, 640; 901/44
See application file for complete search history.

(56) References Cited

U.S. PATENT DOCUMENTS

| | | | | |
|---|---|---|---|---|
| 3,824,843 A * | 7/1974 | Gebeshuber | ........... | G21C 17/00 310/336 |
| 4,146,967 A * | 4/1979 | Rohner | ................ | G01B 5/0002 33/530 |
| 4,166,395 A * | 9/1979 | Dannehl | .............. | G01N 29/265 376/252 |
| 4,600,228 A * | 7/1986 | Tarbuck | ................. | B65G 47/91 228/5.5 |
| 4,612,808 A * | 9/1986 | McKirdy | ............. | G01N 29/265 73/622 |
| 4,715,228 A * | 12/1987 | Livsey | .................... | G01D 11/30 73/583 |
| 4,875,614 A * | 10/1989 | Cipolla | .................. | B23K 20/02 228/44.7 |
| 4,934,671 A * | 6/1990 | Laninga | ............... | B23Q 1/5443 269/20 |

(Continued)

*Primary Examiner* — Lisa Caputo
*Assistant Examiner* — Tran M Tran
(74) *Attorney, Agent, or Firm* — Ostrager Chong Flaherty & Broitman P.C.

(57) ABSTRACT

A mechanism for adjusting the orientation of an end effector (e.g., a non-destructive inspection sensor) during movement over a contoured surface, comprising: (1) a pneumatic or spring-loaded plunger shaft that facilitates positioning of an end effector onto a highly contoured surface by allowing a wide range of vertical motion; (2) a rocker pivotably coupled to a distal end of the plunger shaft, the rocker being pivotable about a horizontal axis to allow a pair of follower wheels coupled to distal ends of the rocker arms to follow the contoured surface and keep the end effector oriented correctly relative to the surface without tipping over; and (3) a hozzle (i.e., an end effector holder) attached to the rocker for rotation therewith, the end effector being coupled to the hozzle by an elastomeric gasket or a plurality of springs which allow the orientation of the end effector relative to the hozzle to change in response to contact forces.

21 Claims, 7 Drawing Sheets

(56) References Cited

U.S. PATENT DOCUMENTS

| | | | | |
|---|---|---|---|---|
| 5,031,458 | A * | 7/1991 | Young | G01N 29/265 73/618 |
| 5,567,881 | A * | 10/1996 | Myers | G01N 29/225 73/588 |
| 5,576,492 | A * | 11/1996 | Phalin | 73/634 |
| 5,698,787 | A | 12/1997 | Parzuchowski et al. | |
| 5,959,211 | A * | 9/1999 | Wagner | G01B 5/066 73/634 |
| 6,220,099 | B1 * | 4/2001 | Marti | G01N 29/226 73/633 |
| 6,227,501 | B1 * | 5/2001 | Malcolm | B60R 19/483 248/27.3 |
| 6,528,109 | B1 * | 3/2003 | Filev | B05B 12/084 118/313 |
| 6,626,834 | B2 * | 9/2003 | Dunne | B06B 1/04 244/3.16 |
| 6,829,959 | B2 * | 12/2004 | Gifford | G01N 27/902 73/577 |
| 7,159,477 | B2 * | 1/2007 | Edwin | G01B 7/281 33/501.08 |
| 7,231,826 | B2 | 6/2007 | Bossi et al. | |
| 7,240,556 | B2 | 7/2007 | Georgeson et al. | |
| 7,249,512 | B2 * | 7/2007 | Kennedy | G01N 29/225 73/618 |
| 7,315,609 | B2 | 1/2008 | Safai et al. | |
| 7,337,673 | B2 | 3/2008 | Kennedy et al. | |
| 7,392,720 | B2 * | 7/2008 | Howarth | G01N 3/48 73/661 |
| 7,499,811 | B2 * | 3/2009 | Migda | G01N 21/57 702/33 |
| 7,562,593 | B2 * | 7/2009 | Engelbart | G01B 5/0004 73/866.5 |
| 7,617,732 | B2 | 11/2009 | Bui et al. | |
| 7,637,162 | B2 * | 12/2009 | Nelson | G01B 5/0004 73/583 |
| 7,640,811 | B2 * | 1/2010 | Kennedy | G01N 29/265 73/602 |
| 7,698,947 | B2 | 4/2010 | Sarr | |
| 7,967,549 | B2 * | 6/2011 | Geist | B25J 9/06 414/744.5 |
| 8,185,240 | B2 * | 5/2012 | Williams | B25J 9/0009 700/159 |
| 8,191,422 | B2 * | 6/2012 | Maruyama | B23Q 35/04 73/633 |
| 8,196,471 | B2 * | 6/2012 | Han | A61B 8/12 600/445 |
| 8,347,746 | B2 * | 1/2013 | Hafenrichter | G01M 5/0016 73/865.8 |
| 8,683,882 | B2 * | 4/2014 | Jackson | G01N 29/24 73/633 |
| 8,738,226 | B2 * | 5/2014 | Troy | B25J 5/007 701/1 |
| 8,841,823 | B2 * | 9/2014 | Jackson | G01N 29/28 310/311 |
| 2006/0043303 | A1 | 3/2006 | Safai et al. | |
| 2009/0038398 | A1 | 2/2009 | Lavoie et al. | |
| 2013/0211782 | A1 * | 8/2013 | Rosenberg | B25J 9/16 702/182 |
| 2014/0182479 | A1 * | 7/2014 | Hafenrichter | B64F 5/0045 105/30 |

\* cited by examiner

APPARATUS FOR AUTOMATED RASTERING OF AN END EFFECTOR OVER AN AIRFOIL-SHAPED BODY

BACKGROUND

The present disclosure relates generally to the field of automated maintenance (including non-destructive inspection) of aircraft structural elements such as airfoil-shaped bodies, and more particularly to an automated end effector-carrying apparatus that is coupled to and travels along an airfoil-shaped body having a relatively short chord length, such as a rotorcraft blade, an aircraft propeller blade, a winglet, a projectile fin, an aircraft horizontal stabilizer, etc., while performing a maintenance function. As used herein, the term "maintenance" includes, but is not limited to, operations such as non-destructive inspection (NDI), drilling, scarfing, grinding (e.g., to remove bonded or bolted components), fastening, appliqué application, ply mapping, depainting, cleaning and painting.

In order to provide maintenance for airfoil-shaped bodies such as blade components, it is known to manually remove the blade components from the aircraft and then manually perform the maintenance functions. Removal of blade components from an aircraft is cost intensive. With helicopter blades, for example, the time spent removing, transporting, re-attaching, balancing and trimming the blades can be significant. Some helicopters require that the blades be removed and inspected every 50-75 flight hours, resulting in a dramatically reduced mission capability of the aircraft.

Furthermore, performing maintenance functions manually uses skilled technicians. These technicians are in short supply; therefore the labor cost to manually perform maintenance functions is significant. Because manual maintenance is complex and repetitive, the likelihood of human error is high. When a repetitive maintenance operation is botched by a human, the flawed blade component could be reattached to the aircraft with a dangerous flaw still imbedded in the component.

Surface-riding probes in gimbaled holders have been used in the non-destructive inspection of composite aerospace hardware in some gantry-type systems. These systems generally use some level of "teaching" of the scanner to get close enough to the contour, and the gimbaling of the shoe handles the difference. They are usually using pulse-echo ultrasound, so the sensor or riding shoe can rest directly on the surface. Besides requiring "teaching", these probes/shoes do not handle significant contours—like those on a rotorcraft blade leading edge—very well. One known scanning system has a spring-loaded shoe that works well for minor contours, but will not work for rotorcraft blades, particularly with sensors that have "feet" on them, because they tend to tip over.

Another apparatus for providing automated movement of a non-destructive inspection (NDI) sensor over a surface of an airfoil-shaped body is disclosed in U.S. Pat. No. 8,347,746. The apparatus in accordance with one embodiment comprises a "blade crawler" that travels in a spanwise direction along a rotorcraft blade. The blade crawler in turn has means for moving an NDI sensor in a chordwise direction. The respective movements in the spanwise and chordwise directions enable the sensor to be rastered over the surface of the rotorcraft blade.

The foregoing "blade crawler" automates what has been a slow and tedious hand-held inspection operation for rotorcraft blades, while allowing the rotorcraft blades to remain on the rotorcraft. However, there are challenges with automated rastering of a sensor on a non-planar surface such as the surface of a rotorcraft blade. While aircraft wings and fuselages have gradual contours, rotorcraft blades have surfaces with more significant contours that may use new fixturing if automation is to be achieved. In addition, the optimum sensors for some rotorcraft blade inspection are pitch-catch sensors, which have several individual "contact feet" on them that make them prone to falling over.

It would therefore be highly desirable to have an automated apparatus capable of scanning airfoil-shaped bodies having short chord lengths and significant contours while adjusting the orientation of the end effector (e.g., an NDI sensor or sensor array) during movement over the contoured surface.

SUMMARY

The subject matter disclosed herein is an automated apparatus for performing maintenance functions on airfoil-shaped bodies having short chord lengths, without the necessity of removing the airfoil-shaped body from the aircraft. There are a number of types of blade components on aircraft that will benefit from maintenance automation, including helicopter blades, propeller blades, flaps, ailerons, trim tabs, slats, stabilators and stabilizers.

In accordance with one embodiment, the apparatus comprises a blade crawler capable of supporting any one of a plurality of end effectors for performing a set of maintenance functions on an airfoil-shaped body such as a blade component. Included in these maintenance functions are multiple options for non-destructive inspection, drilling, grinding, fastening, appliqué application, scarfing, ply mapping, depainting, cleaning, and painting devices that are attached as the end effector for the blade crawler. The blade crawler is movable in a spanwise direction and comprises a traveling element (e.g., a slider) that is linearly translatable in a chordwise direction when the spanwise-movable blade crawler is stationary. A selected one of a plurality of end effectors can be attached to the traveling element. In accordance with each maintenance operation, the selected end effector can be moved in a chordwise direction when the blade crawler is not moving in the spanwise direction. As the end effector moves over a contoured (i.e., non-planar) surface of an airfoil-shaped body, the end effector is compliantly supported by mechanisms that allows the sensor to adjust its height and orientation in response to changes in inclination of the contacting portion of the contoured surface. The height- and orientation-adjustment mechanisms maintain proper alignment and sufficient contact pressure while preventing end effector detachment due to tipping. It also provides a means for damage prevention and movement back to neutral, should the end effector hit an obstruction during rastering. The disclosed apparatus can be used with various NDI sensors used for aerospace structural inspection, including pitch-catch ultrasonic, pulse echo ultrasound, resonance ultrasound, and eddy current.

In accordance with various embodiments, the apparatus comprises a platform, an end effector selected from a group of interchangeable end effectors and carried by the platform, means for mounting the end effector-carrying platform on an airfoil-shaped body, means for moving the end effector-carrying platform in a spanwise direction along the airfoil-shaped body, means for moving the end effector in a chordwise direction relative to the airfoil-shaped body when the platform is stationary, and means for adjusting the orientation of the end effector during movement over the contoured surface.

One aspect of the subject matter disclosed herein is a mechanism comprising: a support member; a plunger shaft that is supported by and has a range of vertical motion relative to the support member; a rocker pivotably coupled to a distal end of the plunger shaft, the rocker being pivotable about a horizontal axis and comprising first and second arms, and first and second follower wheels pivotably coupled to respective distal ends of the first and second arms; an end effector holder attached to or integrally formed with the rocker for rotation therewith; an end effector; and means for coupling the end effector to the end effector holder in a manner that allows the end effector to tilt relative to the end effector holder in any direction in response to forces exerted on the end effector and then urges the end effector toward an untilted position when the forces are removed. The end effector may comprise a non-destructive inspection sensor or sensor array, such as a pitch-catch sensor, or a different maintenance tool. The mechanism may further comprise means for urging the plunger shaft to move downward relative to the support member.

Another aspect of the disclosed subject matter is a mechanism comprising: a support member; a plunger shaft that is supported by and has a range of vertical motion relative to the support member; a rocker pivotably coupled to a distal end of the plunger shaft, the rocker being pivotable about a horizontal axis and comprising first and second arms, and first and second follower wheels pivotably coupled to respective distal ends of the first and second arms; an effector holder attached to or integrally formed with the rocker for rotation therewith, the effector holder comprising a ring-shaped portion; an end effector surrounded by the ring-shaped portion of the end effector holder; and an elastomeric gasket having an inner perimeter attached to the end effector and an outer perimeter attached to the ring-shaped portion of the end effector holder, wherein the end effector is suspended within the ring-shaped portion of the end effector holder by the elastomeric gasket. Preferably the elastomeric gasket has sufficient elasticity to allow the end effector to tilt relative to the end effector holder in any direction in response to forces exerted on the end effector and then urge the end effector toward an untilted position when the forces are removed.

A further aspect is a mechanism comprising: a support member; a plunger shaft that is supported by and has a range of vertical motion relative to the support member; first elastomeric or spring means coupled to a distal end of the plunger shaft; a rocker coupled to and depending from the first elastomeric or spring means, the rocker comprising first and second arms, and first and second follower wheels pivotably coupled to respective distal ends of the first and second arms; an end effector holder attached to or integrally formed with the rocker for movement therewith; an end effector; and second elastomeric or spring means for coupling the end effector to the end effector holder, wherein the rocker is able to tilt relative to the plunger shaft and the end effector is able to tilt relative to the end effector holder.

A further aspect of the subject matter disclosed herein is an automated apparatus for moving a mechanism (of a type as described in the preceding three paragraphs) over a surface of an airfoil-shaped body. This automated apparatus comprises: a chassis adapted to travel along an airfoil-shaped body in a spanwise direction; a guide element mounted to the chassis, the guide element being disposed in a chordwise direction; and a slider element slidably coupled to and movable along the guide element. The support member of the mechanism is attached to or integrally formed with the slider element. The apparatus may further comprise a first actuator for moving the chassis in the spanwise direction, a second actuator for moving the slider element in the chordwise direction, and a computer system which is programmed to activate the first and second actuators at different times to produce rastering of the end effector. In addition, the apparatus may further comprise a position tracking system which tracks the position of the end effector during rastering motion.

Yet another aspect is an automated apparatus for moving an end effector over a surface of an airfoil-shaped body, comprising: a chassis adapted to travel along an airfoil-shaped body in a spanwise direction; a first actuator for moving the chassis in the spanwise direction; a guide element mounted to the chassis, the guide element being disposed in a chordwise direction; a slider element slidably coupled to and movable along the guide element; a second actuator for moving the slider element in the chordwise direction; a support member attached to or integrally formed with the slider element; a plunger shaft that is supported by and has a range of vertical motion relative to the support member; a rocker pivotably coupled to a distal end of the plunger shaft, the rocker being pivotable about a horizontal axis and comprising first and second arms, and first and second follower wheels pivotably coupled to respective distal ends of the first and second arms; an end effector holder attached to or integrally formed with the rocker for rotation therewith; an end effector that is tiltable relative to the end effector holder; and a computer system which is programmed to activate the first and second actuators at different times to produce rastering of the end effector. The apparatus may further comprise means for coupling the end effector to the end effector holder in a manner that allows the end effector to tilt relative to the end effector holder in any direction in response to forces exerted on the end effector and then urges the end effector toward an untilted position when the forces are removed; means for urging the plunger shaft to move downward relative to the support member; and means for urging the rocker toward a neutral position in response to the rocker adopting a non-neutral position.

Other aspects are disclosed and claimed below.

BRIEF DESCRIPTION OF THE DRAWINGS

Reference will hereinafter be made to the drawings in which similar elements in different drawings bear the same reference numerals.

DETAILED DESCRIPTION

The subject matter disclosed in detail hereinafter is directed to an autonomous, self-propelled, expandable and adjustable apparatus for inspecting in-service airfoil-shaped structures such as rotorcraft blades, aircraft propellers, smaller winglets, and narrow tail sections for structural damage by crawling along the length of the airfoil-shaped structure (i.e., in a spanwise direction) using the structure itself as the track. The apparatus carries a non-destructive inspection (NDI) sensor that scans the airfoil-shaped structure in a direction normal to the longitudinal axis of the airfoil-shaped structure (i.e., in a chordwise direction). The NDI sensor carried by the apparatus can be a pitch-catch ultrasonic or other low-frequency sensor, pulse echo ultrasonic sensor, resonance ultrasonic sensor, an eddy current sensor, mechanical impedance analysis sensor, mechanical tap tester, micro- or millimeter-wave sensor, capacitive sensor, thermographic sensor, or shearographic sensor. The NDI sensor acquires data representing the structural conditions found as the inspection apparatus moves across the surface of the airfoil-shaped structure. Multiplexed pulser/receiver cards, and a controller within a computer with imaging software, can be electrically coupled to the expandable crawler portion of the system by means of a cable to collect, display, and store NDI data.

Figure 1:
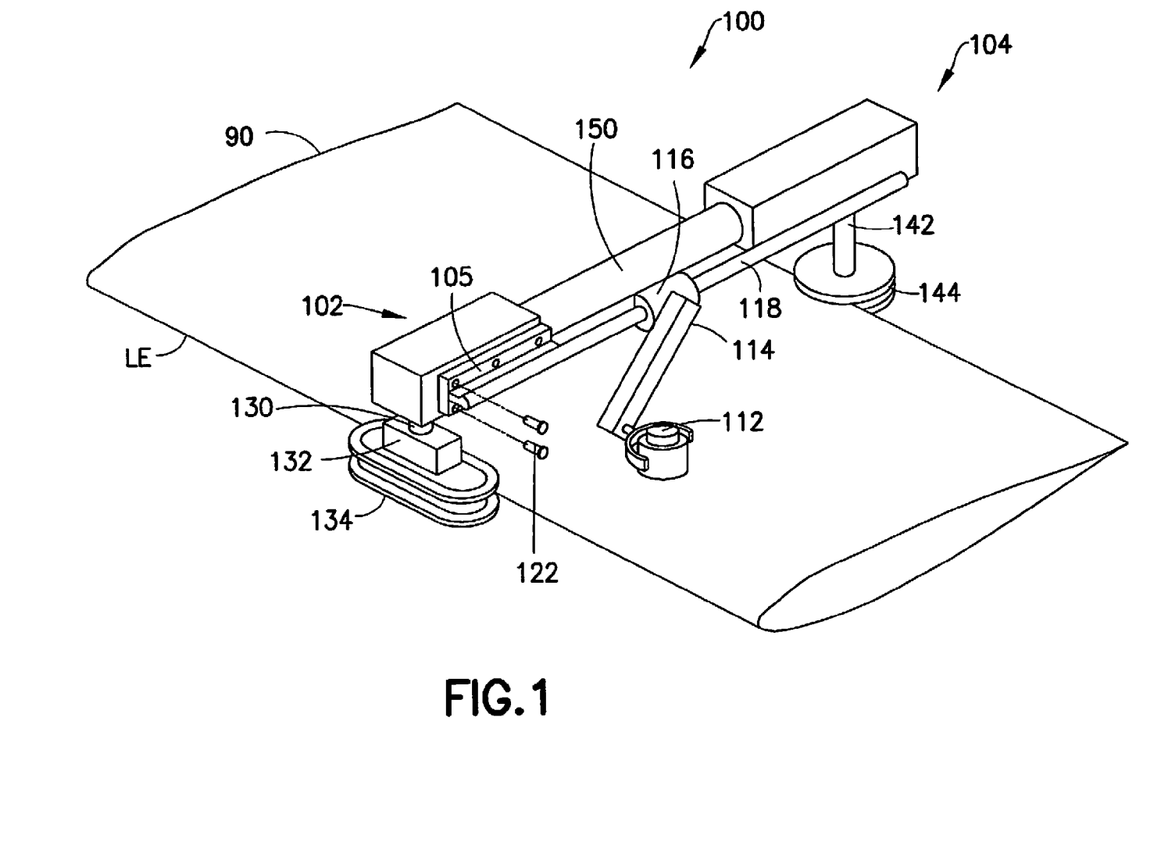
FIG. 1 is an isometric view of a blade crawler mounted on an airfoil structure having a short chord length and a significant contour, the blade crawler being movable in a spanwise direction and carrying a gimbaled NDI sensor which can be moved in a chordwise direction.

As seen in FIG. 1 an inspection apparatus 100 (hereinafter referred to as a "crawler") comprises a forward body part 102, a rearward body part 104, and an intercostal element 150 that interconnects the forward and rearward body parts to form a chassis. One of the forward and rearward body parts is displaceable along an axis of the intercostal element to facilitate adjustment of the distance separating the forward and rearward body parts, while the other body part is fixed relative to the intercostal element. For example, the intercostal element 150 may comprise a circular cylindrical tube or rod having one end fixed to the forward body part 102, while a portion extending from the other end has the rearward body part 104 slidably mounted thereon in the manner of a telescoping sleeve, allowing the distance between the forward and rearward body parts to be adjusted to adapt to airfoil-shaped bodies having different chord lengths.

The forward body part 102 is positioned near a forward (i.e., leading) edge of the airfoil-shaped body 90 that is to be inspected, and the rearward body part 104 is positioned near an opposing (i.e., trailing) edge of the structure to be inspected. Inspection of the airfoil-shaped body 90 is carried out, in part, by a sensor 112 pivotally mounted on one end of an arm 114, the other end of the arm 114 in turn being pivotably mounted to a slider 116 coupled to and slidable on a guide rod 118. (Alternatively, a guide rail or other guide element could be used in place of a guide rod.) The guide rod 118 is integrally formed with a mounting plate 105 that is fastened to the forward body part 102 by a plurality of fasteners 122. The sensor 112 may comprise any one of a variety of NDI sensors to perform inspection of the airfoil-shaped body 90.

In accordance with one embodiment, sensor 112 follows the curved surface of the airfoil-shaped body 90 when arm 114 exerts a normal force on the pivotably supported sensor 112. The normal force keeps the scanner in intimate contact with the airfoil surface, thus enabling the NDI functionality of the scanner. In cases where the scanner comprises an array of ultrasonic transducers, acoustic couplant may be supplied from the operations center to the interface of the scanner and airfoil, for example, via a hose. The normal force exerted by the arm 114 can be generated by any conventional means, including the coupling of a spring, solenoid, pneumatic actuator or radial motion transducer (not shown in FIG. 1) between arm 114 and slider 116.

The forward body part 102 has a first rod 130 depending therefrom on which is mounted a control motor 132. A drive wheel (not shown) is operatively connected to and supported from the control motor 132, the latter causing a drive track 134 to circulate around the drive wheel and a second wheel (also not shown) while drive track 134 stays in frictional contact with the leading edge (LE in FIG. 1) of the airfoil-shaped body 90. Rotation of rod 130 causes the crawler 100 to travel in a spanwise direction provided that the drive track 134 does not slip relative to the leading edge.

Still referring to the embodiment depicted in FIG. 1, a second rod 142 depends from the rearward body part and carries a follower encoder wheel 144 on the free end thereof. The spanwise position of crawler 100 is measured by a rotary encoder (incorporated in the rearward body part 104), which encodes rotation of encoder wheel 144. The encoder wheel 144 rides on the airfoil surface as the crawler travels in the spanwise direction. The rotary encoder sends an encoder pulse to the operations control center (e.g., via an encoder cable or a wireless connection) after each incremental movement of crawler 100 in the spanwise direction, which encoder pulses are used by a control computer (not shown in FIG. 1, but see item 50 in FIG. 7, to be described in detail later) and by ultrasonic pulser/receiver devices (not shown in the drawings) to determine the spanwise coordinate of each scan plane in a well-known manner.

The drive track 134 and the encoder wheel 144 are held against, and in frictional engagement with, the leading and trailing edges, respectively, of the airfoil-shaped body 90 to be inspected. This is accomplished by application of a tensile force imparted to the forward and rearward body parts 102, 104 (to be discussed below). The front and rearward body parts in turn (in response to the tensile force applied between the front and rearward body parts) apply a compressive force on the blade component (via the drive track 134 and encoder wheel 144) that holds the crawler on the blade component. Preferably, drive track 134 is made of a material that frictionally engages the leading edge of the structural part being inspected so as to impart a driving force that moves the crawler 100 spanwise along the airfoil-shaped body 90. Additionally, the encoder wheel 144 tracks the spanwise position of the crawler 100 as it translates along the airfoil-shaped body 90.

The rearward body part 104 carries encoder wheel 144, which depends from, and is attached to, the rearward body part on a telescoping rod 142 that allows the vertical position of the encoder wheel to be adjusted to fit the trailing edge of the airfoil-shaped body 90. The drive track 134 and encoder wheel 144, in conjunction, exert a gripping force on the airfoil-shaped body 90 that holds the crawler 100 thereon. A sufficient gripping force is generated when the telescoping sleeve (i.e., the rearward body part 104) retracts, causing the drive track 134 to engage the leading edge and the encoder wheel 144 (which also functions as an alignment wheel) to engage the trailing edge. Any one of a multiplicity of known linear motion devices (not shown) can be employed to cause the rearward body part 104 to retract relative to the intercostal element 150, including the following: a solenoid, a piston, a rack and pinion assembly, a spring, or other translation mechanism. For example, the gripping force can be generated by a spring which extends between the intercostal element 150 and the rearward body part 104. In accordance with one embodiment, the spring has opposing ends attached to (for applying a tensile force between) the rearward body part 104 and to one of a plurality of attachment points spaced along the length of the intercostal element 150.

Various types of sensors may be utilized to perform non-destructive testing. One or more sensors may move over the portion of the structure to be examined, and receive data regarding the structure. For example, a pulse-echo, thru-transmission, or shear wave sensor may be utilized to obtain ultrasonic data, such as thickness gauging, detection of laminar defects and porosity, and/or detection of cracks in the structure. Resonance, pitch/catch or mechanical impedance sensors may be utilized to provide indications of voids or porosity, such as in adhesive bondlines of the structure. In addition, single and dual current eddy current sensors impart and detect eddy currents within a structure so as to identify cracks and/or corrosion, particularly in metallic or other conductive structures. In accordance with various alternative embodiments, the sensors may comprise mechanical impedance analysis sensors, mechanical tap testers, micro- or millimeter-wave sensors, capacitive sensors, thermographic sensors, or shearographic sensors. The data acquired by the sensors is typically processed by a processing element, and the processed data may be presented to a user via a display in a conventional manner.

Referring again to FIG. 1, to translate the sensor 112 chordwise across the airfoil-shaped body 90, it is contemplated that a motor (not shown) will be encased within the slider 116 to interact with the guide rod 118 via gears or friction wheels (also not shown). Alternatively, the chordwise motion may be achieved by positioning the motor on the forward body part 102 and translating the slider 116 via a cable, drive belt, chain, or screw-drive in a well-known manner.

As described previously, a tensile force can be applied by an internal tension spring that extends between an attachment point (not shown) on the intercostal element 150 and an attachment point (not shown) on the movable rearward body part 104. Multiple attachment points can be provided on the intercostal element 150 so that a spring tension within desired operational limits can be maintained during respective inspections of blades having different chord lengths. When one end of the tension spring is unlocked from a current attachment point, the rearward body part 104 can be translated along the intercostal element 150 in either direction and then the tension spring can be hooked onto a new attachment point, selected to produce a desired spring tension. In this manner, the crawler 100 can be expanded or retracted to accommodate structural elements having a range of chord lengths.

The drive track 134 shown in FIG. 1 can be replaced by a drive roller operatively coupled to the control motor 132 (carried by forward body part 102) and a secondary follower wheel displaced spanwise from the drive wheel (also carried by forward body part 102).

The sensor 112 can be indexed in a conventional manner, taking measurements (e.g., ultrasonic scanning in a scan plane) at the initial position and each incremental position thereafter until the final position is reached. The position of slider 116 relative to the guide rod 118 can be measured by a second encoder (not shown in FIG. 1) incorporated in the motor that drives slider travel along the guide rod. The relationship of slider position (relative to the guide rod) to scanner position (relative to the airfoil) can be determined empirically and used by the control computer to determine the scanner position as a function of the pulses from the second encoder, which encoder pulses are used by a control computer and by the ultrasonic pulser/receiver devices to determine the chordwise coordinates of the acquired scan data. Alternatively, an encoder wheel could be mounted to the scanner in a manner such that it rolls along the airfoil surface as the sensor 112 is moved in a chordwise direction.

Figure 7:
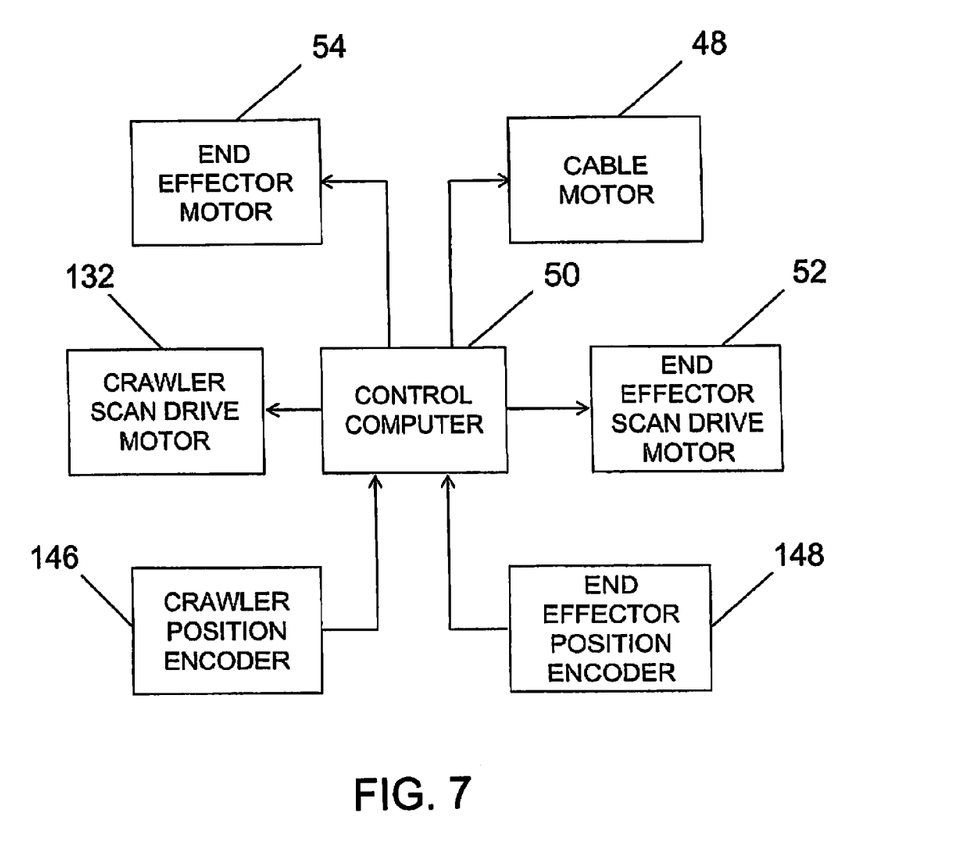
FIG. 7 is a block diagram showing communications between a control computer and various components of a blade crawler in accordance with one embodiment.

Data developed by the sensor 112 and the positional encoding mechanisms is fed as analog or digital signals to a central computer (item 50 in FIG. 7). The resulting output of the central computer can then be fed to a display device, such as a computer-driven display, thereby permitting an operator to view results being obtained. This visual information gives an operator the opportunity to make appropriate adjustments to the scanner apparatus to ensure the desired scanning information is being obtained.

The blade crawler described above can also be adapted for use in the automation of various maintenance functions, including but not limited to non-destructive inspection, drilling, grinding, fastening, appliqué application, scarfing, ply mapping, depainting, cleaning and painting. There are a number of types of blade components on aircraft that will benefit from maintenance automation, including helicopter blades, propeller blades, flaps, ailerons, trim tabs, slats, stabilators and stabilizers. These operations enable the blade crawler to reduce maintenance time, reduce maintenance labor and reduce human error—all through automation of these normally manual processes.

Figure 2:
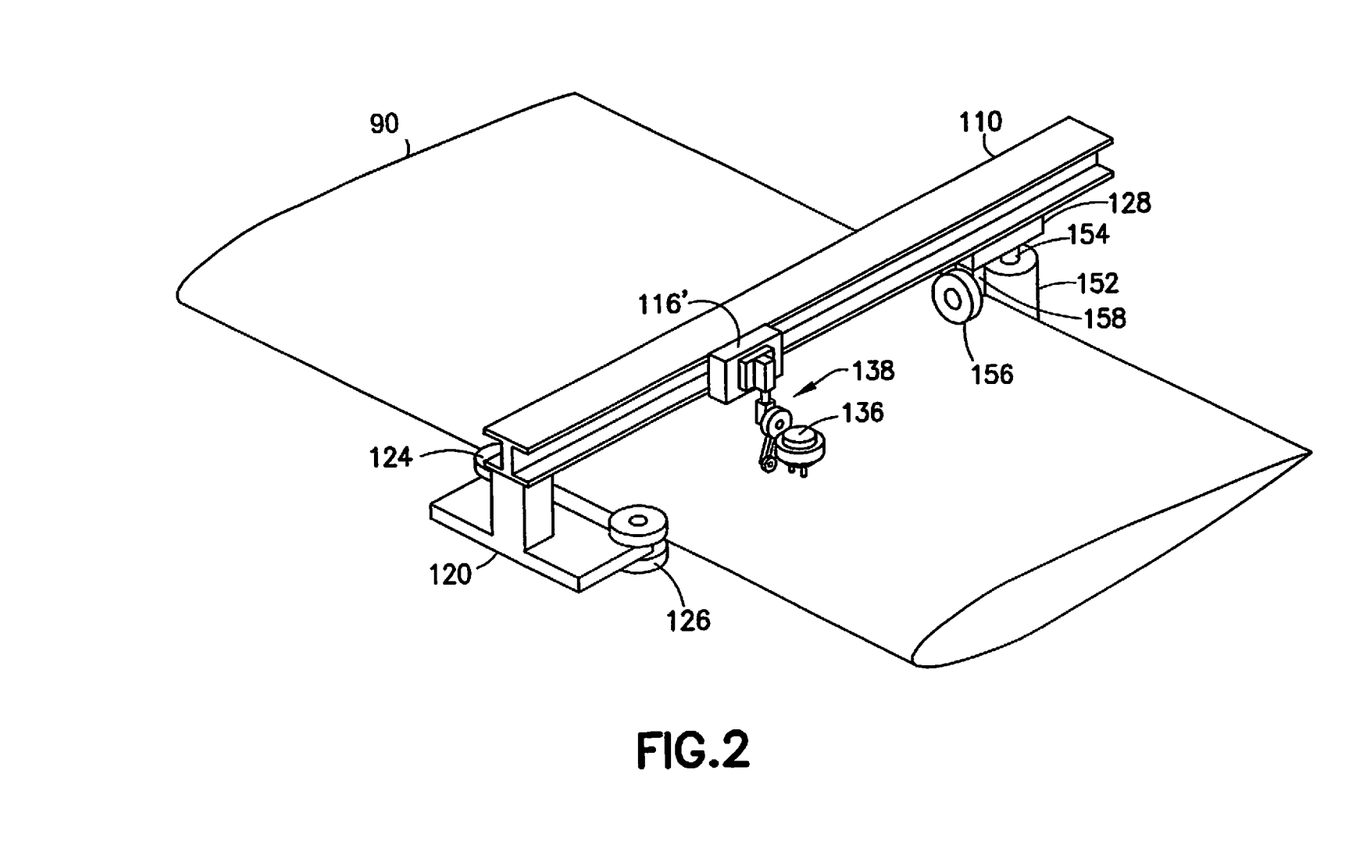
FIG. 2 is an isometric view of a blade crawler which improves upon the blade crawler depicted in FIG. 1, this improved blade crawler comprising a probe support assembly that allows an NDI sensor to adjust its orientation during movement over a contoured surface. For the sake of simplicity, means for exerting a gripping force on the airfoil structure and means for chordwise scanning of the NDI sensor are not shown.

FIG. 2 shows an inspection apparatus having an improved mechanism for adjusting the orientation of the end effector during movement over the contoured surface of an airfoil-shaped body. For the sake of simplicity, the means for exerting a gripping force on the airfoil structure and the means for chordwise scanning of the sensor probe are not shown, but those means may comprise mechanisms similar to those depicted in FIG. 1. The inspection apparatus may comprise a forward body part 120, a rearward body part 128, and an intercostal element 110 that interconnects the forward and rearward body parts to form a chassis. For example, the intercostal element 110 may comprise a rigid I-beam having a guide rod mounted thereto (similar to guide rod 118 depicted in FIG. 1, but not shown in FIG. 2). The forward body part 120 is positioned near a forward (i.e., leading) edge of the airfoil-shaped body 90 that is to be inspected, and the rearward body part 128 is positioned near an opposing (i.e., trailing) edge of the structure to be inspected. Alternatively, the I-beam can be used like a rail such that the I-beam serves as a guide rod. In this configuration, the tips of the I-beam may have a bulbous cross section so that the slider can grab onto the edges of the I-beam.

The chassis further comprises a drive wheel 124 and a follower wheel 126, both pivotably mounted to the forward body part 120, and a follower wheel 152 mounted on the distal end of a shaft 154 which is pivotably coupled to the rearward body part 128. Wheels 124, 126 and 152 allow the chassis to travel in a spanwise direction along the length of the airfoil-shaped body 90. The drive wheel 124 may be driven by a motor (not shown). A rotary encoder 158, mounted to rearward body part 128, is coupled to an encoder wheel 156 that rolls on the workpiece surface. The spanwise position of the crawler is measured by rotary encoder 158, which encodes rotation of encoder wheel 156 as the latter rolls on the airfoil surface during spanwise travel of the crawler. The rotary encoder 156 sends an encoder pulse to the operations control center (e.g., via an encoder cable or a wireless connection) after each incremental movement of the crawler in the spanwise direction, which encoder pulses are used by the control computer and by ultrasonic pulser/receiver devices to determine the spanwise coordinate of each raster line in a well-known manner.

In accordance with the embodiment depicted in FIG. 2, inspection of the airfoil-shaped body 90 is carried out by a pitch-catch sensor 136 comprising two piezoelectric transducers mounted in a pitch-catch arrangement. One transducer transmits an ultrasonic signal and the other receives the signal returned from the airfoil-shaped body 90. The pitch-catch sensor 136 is supported by a probe support assembly 138 which depends from a slider 116'. The slider 116' may be coupled to and slidable on a guide rod (not shown in FIG. 2, but see item 118 in FIG. 1) or a guide rod. A motor (not shown) will be encased within the slider 116' to interact with the guide rail or guide rod via gears or friction wheels (also not shown). An encoder wheel (not shown) can be pivotably coupled to the slider 116', which encoder wheel in turn may be coupled to a rotary encoder that outputs pulses representing incremental chordwise motion of the probe support assembly 138 along the length of the intercostal element 110. As the pitch-catch sensor 136 is moved in a chordwise direction (while the chassis is not moving in the spanwise direction), the probe support assembly 138 allows the orientation of the sensor to adjust to the inclination of the contacting portion of the contoured surface of the airfoil-shaped body 90. In particular, the orientation of the pitch-catch sensor 136 is adjusted so that its contact feet 140 both remain in contact with the contoured surface.

Figure 3:
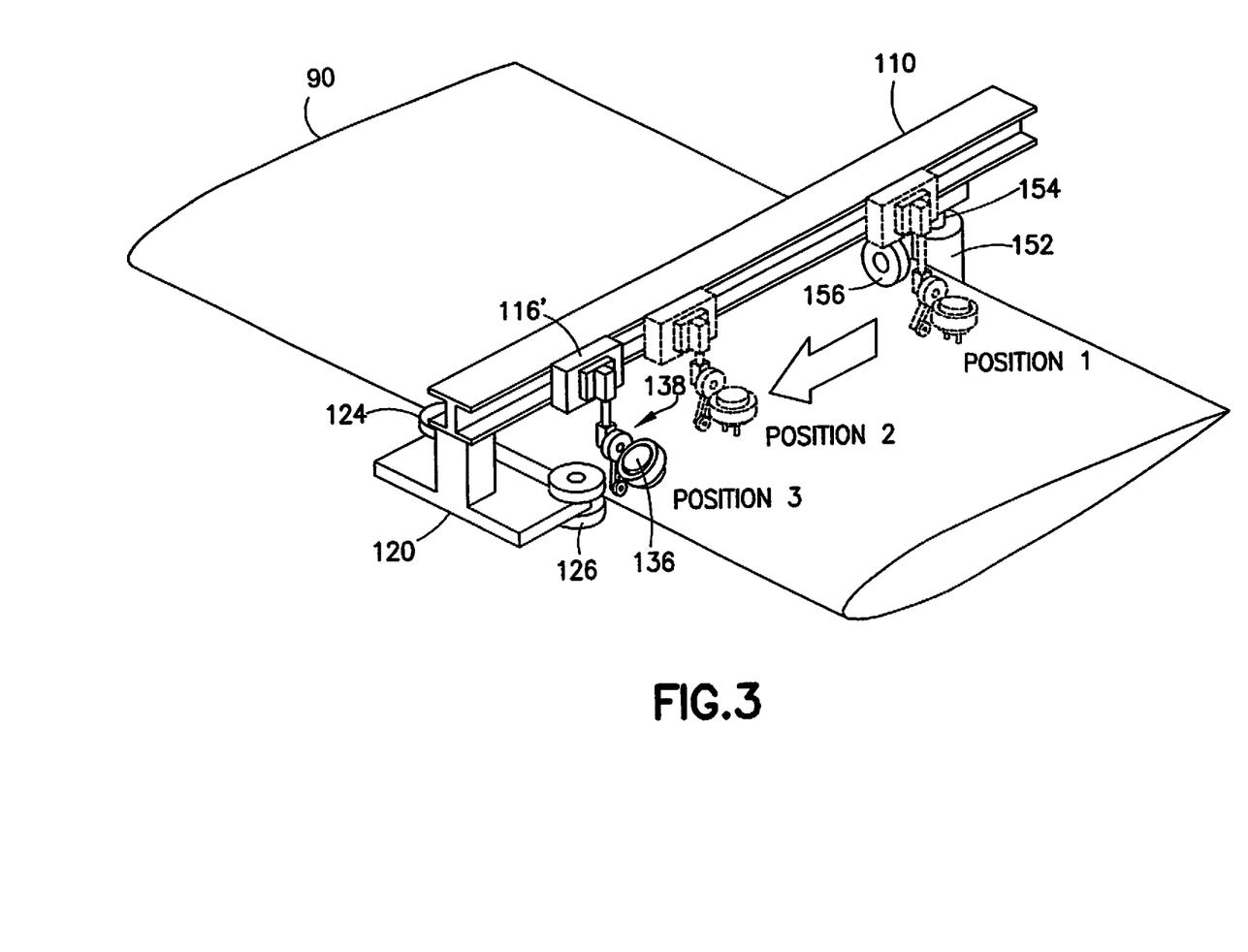
FIG. 3 is an isometric view of the same blade crawler depicted in FIG. 2, with probe support assembly being shown in three different raster positions.

FIG. 3 shows the probe support assembly 138 in three positions spaced apart in the chordwise direction. As the probe assembly moves from position 1 to position 2 (which motion is indicated by an arrow in FIG. 3), the probe support assembly allows the pitch-catch sensor 136 to adjust its orientation to be normal to the contacting portion of the contoured surface. Position 3 shows a situation wherein the pitch-catch sensor 136 is near the leading edge of the airfoil-shaped body 90, which causes the pitch-catch sensor to tilt at a greater angle reflecting the increased angle of inclination of the workpiece surface near its leading edge.

Figures 4, 4A:
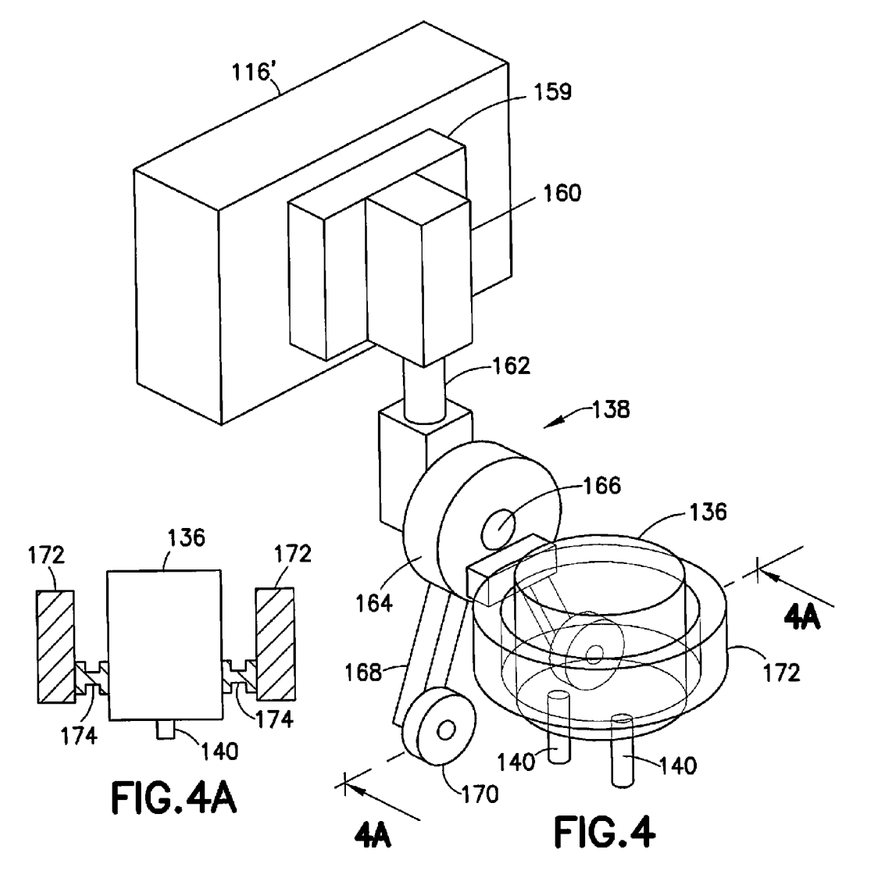
FIG. 4 is a magnified isometric view of the probe support assembly depicted in FIG. 2.
FIG. 4A is a cross-sectional view of the probe support assembly depicted in FIG. 4, the section being taken along line 4A-4A seen in FIG. 4.

Referring to FIG. 4, the probe support assembly 138 comprises a plurality of mechanisms which allow the sensor orientation to adjust automatically as the angle of inclination of the contacting workpiece surface area changes. First, the probe support assembly 138 comprises a plunger housing 160 which is attached to the slider 116' by means of a mounting plate 159. The plunger housing 160 houses a plunger shaft 162 which is displaceable relative to plunger housing 160 in an axial direction, which is aligned with an elevation direction. During an inspection operation, the plunger shaft is urged to displace downwardly, toward the workpiece surface by means of a pneumatic actuator or a spring disposed inside the plunger housing 160. An inverted V-shaped rocker 164 is pivotably coupled to a distal end of the plunger shaft 162 at a pivot point 166 (e.g., a pin joint). (A pin joint is a one-degree-of-freedom kinematic pair used in mechanisms, and is also known as a revolute joint. Pin joints provide single-axis rotation.) Since the pivot point 166 is supported by and coupled to the plunger shaft 162, any vertical movement of the latter will result in an equal vertical movement of the pivot point 166. The axis of pivot point 166 is horizontal and generally aligned with the spanwise direction of the airfoil-shaped body being inspected.

The rocker 164 comprises a pair of arms 168. As seen in FIG. 4, the second arm is behind the pitch-catch sensor 136. A respective follower wheel 170 is pivotably coupled to the distal end of each rocker arm 168. During inspection, the plunger shaft 162 will be displaced downward until both follower wheels 170 come into contact with the contoured workpiece surface. If the surface is planar in the area where the two follower wheels contact, then the rocker 164 will have an angular position of zero degrees. If, however, the surface in the area where the two follower wheels abut the workpiece is at an angle relative to horizontal, then the rocker will adopt a non-zero angular position. This feature allows the follower wheels 170 to follow the contoured surface.

Still referring to FIG. 4, the pitch-catch sensor 136 is held within a hozzle 172 in the shape of an annular ring. The hozzle 172 is rigidly affixed to or integrally formed with a portion of rocker 164 that is disposed under the pivot point 166. Therefore, as the rocker 164 rotates about the horizontal axis of pivot point 166, the hozzle 172 also rotates about the same horizontal axis, causing the sensor 136 to tilt relative to a horizontal plane. In one implementation the ends of the contact feet 140 are disposed in a plane which is tangent to both follower wheels 170 at the points where the latter contact the workpiece. In other words, if the workpiece surface were planar, both follower wheels 170 and both contact feet 140 can contact that planar surface at the same time, which is the situation depicted in FIG. 5A.

Figures 5A, 5B, 5C:
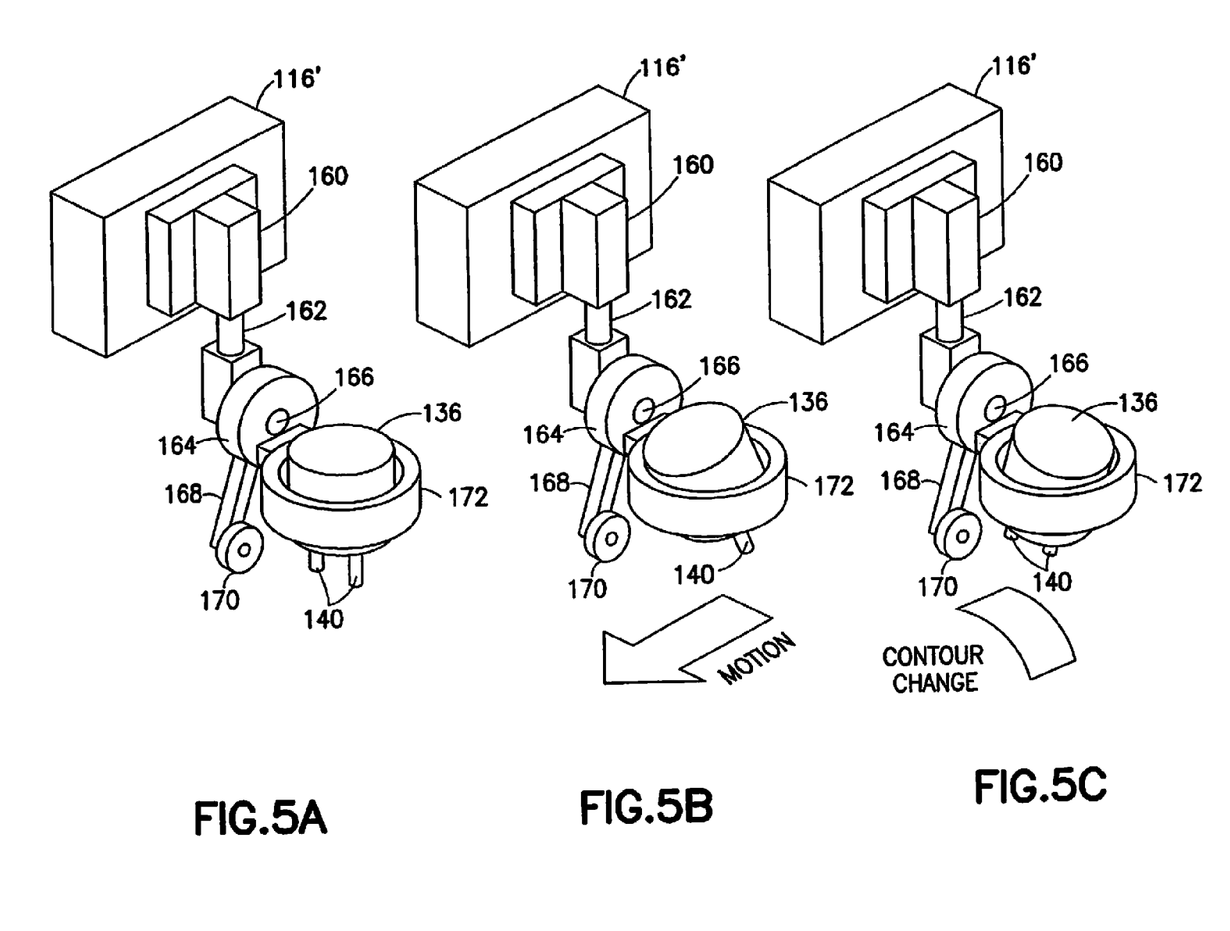
FIGS. 5A through 5C are respective isometric views of the probe support assembly depicted in FIG. 4 in the following scenarios: (1) the NDI sensor is not tilted relative to a vertical axis of a plunger shaft (FIG. 5A); (2) the NDI sensor is tilted relative to a vertical axis of a plunger shaft due to impingement against a bump or other obstruction as the NDI sensor moves in a chordwise direction (FIG. 5B); and (3) the NDI sensor is tilted relative to a vertical axis of a plunger shaft due to a contour change in a spanwise direction (FIG. 5C).

However, referring now to the sectional view of FIG. 4A, it can be seen that, in accordance with one implementation, the outer perimeter of the pitch-catch sensor 136 is connected to the inner perimeter of the hozzle 172 by a gasket 174, which preferably takes the form of an annular membrane made of an elastomeric material, such as any one of a multitude of suitable rubbers (e.g., neoprene). Alternatively, a plurality of springs distributed at equi-angular intervals could be used to couple the sensor to the hozzle. In the case depicted in FIG. 4A, the outer diameter of the pitch-catch sensor 136 is less than the inner diameter of the hozzle 172 by the width of gasket 174, providing a gap which allows the sensor 136 to tilt relative to hozzle 172, independently of the rotation of hozzle 172 about the pivot point 166, as shown in FIGS. 5A and 5B. As seen in FIG. 5B, the elastomeric gasket 174 allows the pitch-catch sensor 136 to traverse minor bumps and handle contours that are perpendicular to the direction of motion (indicated by the arrow in FIG. 5B) during rastering in the chordwise direction. Preferably, the elastomeric gasket has sufficient elasticity to allow the sensor to tilt relative to the hozzle in any direction in response to forces exerted on the sensor and then urge the sensor toward an untilted position when those forces are removed.

In accordance with the same implementation, the sensor 136 is arranged such that the contact feet 140 lie along a hypothetical line which is perpendicular to the chordwise direction of motion of the rocker during rastering, which perpendicular line meets another hypothetical line connecting the follower wheels 170 at a midpoint thereof. Explained differently, the follower wheels and each contact foot are arranged so that their points of contact with a planar surface would be at respective vertices of respective triangles (e.g., isosceles triangles) of different height, the contact feet being located at respective peaks of the respective triangles. In accordance with this geometric arrangement, while the follower wheels 170 are free to follow a first contour in the chordwise direction, the sensor 136 is free to tilt independently to allow its contact feet to follow different contours displaced from but parallel to the first contour. Such a situation could occur in cases where the shapes of chordwise contours at spaced intervals vary in the spanwise direction, as depicted in FIG. 5C.

The pneumatic or spring-loaded plunger shaft 162 of the embodiment depicted in FIGS. 4, 4A, and 5A-5C facilitates positioning of an end effector onto a highly contoured surface by allowing a wide range of vertical motion. The rocker 164 is pivotable about a horizontal axis to allow the arms 168 of the rocker to follow the contoured surface and keep the end effector oriented correctly relative to the surface without tipping over. The hozzle 172 is attached to the rocker 164 for rotation therewith, the end effector being coupled to the hozzle by an elastomeric gasket 174 (or a plurality of springs) which allows the orientation of the end effector relative to the hozzle to change in response to contact forces exerted on the end effector by the contoured surface. The elastomeric gasket or plurality of springs within the hozzle allow the end effector to traverse minor bumps and handle contours that are perpendicular to the raster direction. Optionally, the rocker may incorporate a torsion spring that tends to restore the angular position of the rocker to a "zero" or neutral position to help prevent tip-overs and to maintain orientation at the edges of the airfoil-shaped body (if a rocker arm wheel goes off an edge). In the alternative, the same effect can be achieved by placing respective springs between the plunger shaft and the rocker arms, the springs being arranged to urge the rocker toward its neutral position when the rocker is not in that position.

Figure 6A:
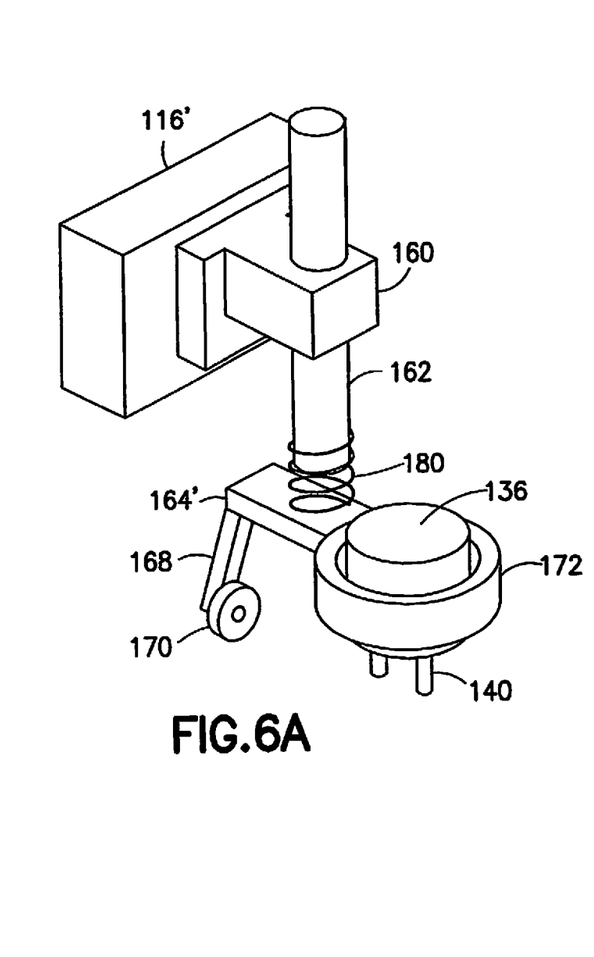
FIGS. 6A and 6B are respective isometric views of a probe support assembly in accordance with an alternative embodiment in the following scenarios: (1) the NDI sensor is not tilted relative to a vertical axis of a plunger shaft (FIG. 6A); and (2) the NDI sensor is tilted relative to a vertical axis of a plunger shaft due to due to a contour change (FIG. 6B).
Figure 6B:
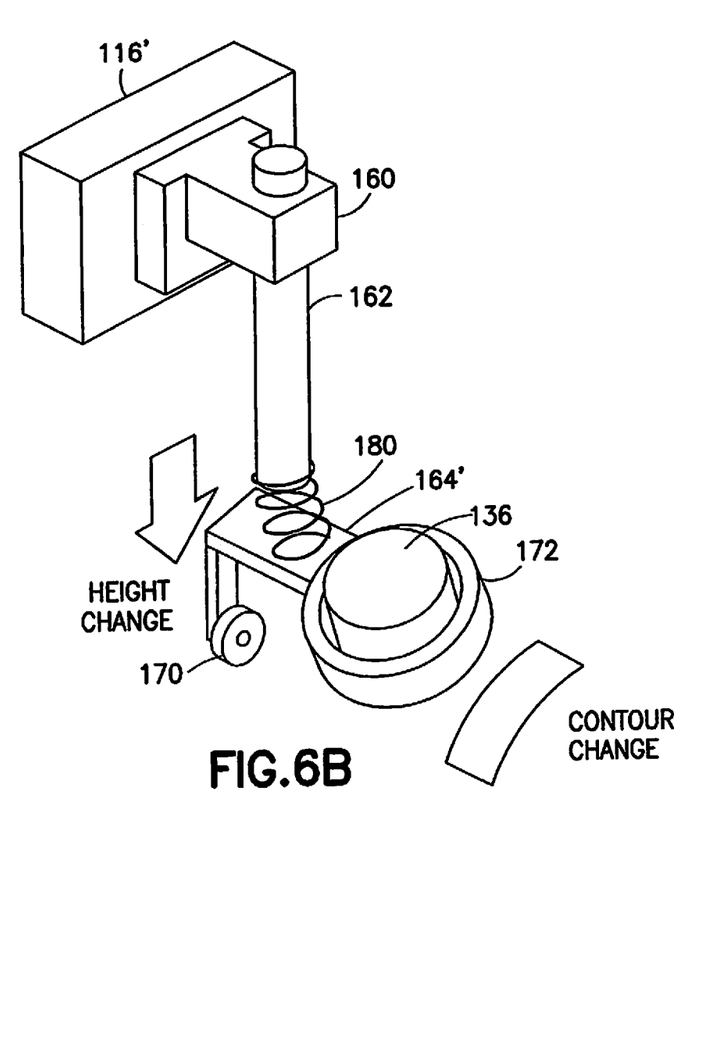

A probe support assembly in accordance with a further alternative embodiment is depicted in FIGS. 6A and 6B. FIG. 6A shows an inspection scenario in which a pitch-catch sensor 136 is not tilted relative to the axis of a plunger shaft 162, while FIG. 6B shows an inspection scenario in which pitch-catch sensor 136 is tilted relative to the axis of plunger shaft 162 due to a change in the contour of the workpiece surface being inspected. In this embodiment, a rocker 164' is coupled to a distal end of a plunger shaft 162 by means of a coil spring 180. Although the second arm and second follower wheel of the rocker 164' are blocked from view in FIGS. 6A and 6B, the rocker 164' preferably has two arms 168, respective follower wheels 170 being pivotably mounted to the distal ends of arms 168. The geometric relationship between the follower wheels 170 and the contact feet 140 of the pitch-catch sensor 136 may be the same as previously described for the embodiment shown in FIGS. 5A-5C. In response to the rocker 164' being deflected away from its neutral position, the coil spring 180 at the end of plunger shaft 162 will exert a spring force that urges rocker 164' toward its neutral position to prevent tip-overs and to maintain orientation at edges (e.g., if a follower wheel 170 were to roll off an edge of the airfoil).

In accordance with another embodiment, the coil spring 189 could be replaced by a bendable connective element made of elastomeric material, such as a rubber material. The upper end of the bendable connective element would be attached to the distal end of the plunger shaft, while the lower end of the connective element would be attached to the rocker.

While the particular embodiments disclosed above incorporate a mechanism that allows the orientation of an NDI sensor to adjust to a changing contour of a workpiece surface, the same mechanism can be used to support end effectors other than NDI sensors or sensor arrays. For example, the disclosed assembly could be used to support a rotary scarfer that is pneumatically driven via a hose supplying pressurized air from an operations center. The spanwise position of the blade crawler, the chordwise position of the rotary scarfer, and the operation of the rotary scarfer (or other end effector) can be controlled by the operations central computer in accordance with a pre-programmed maintenance operation. It is also possible for the system operator to manually control functions by means of a joystick or numeric commands typed on a keyboard.

For many blade components made of laminated composite material, scarfing to eradicate skin damage is a common maintenance function. The automated scarfing involves the removal of material (i.e., auguring) by means of milling using a high-speed rotary bit or mechanical sanding using an abrasive pad. Auguring is often performed in order to prepare a component surface for a hot bond repair. For example, plies of composite material could be removed in a damaged area to form a cavity suitable for receiving a stack of plies of composite material designed to form a repair patch when cured in place. Alternatively, a grinding tool could be substituted for the rotary scarier for removing bonded or bolted components.

For many blade components, ply mapping as a prelude to the application of a repair patch is a common maintenance function. A ply mapper may comprise a digital photographic device or a touch probe device to define the shape of the cavity formed during the scarfing operation. The goal is to acquire a three-dimensional measurement of the cavity, including measurements indicating the shape of the cavity and lateral dimensions of the cavity at various depths. Based on this information, plies having the appropriate shape and lateral dimensions can be cut and stacked in the cavity for creating a repair patch.

FIG. 7 is a block diagram showing communications between a control computer 50 and various components of an end effector-carrying blade crawler in accordance with a further embodiment. In this instance, the control computer 50 is connected to the blade crawler by an electrical cable (not shown). (Alternatively, the control computer and the blade crawler could communicate wirelessly.) The control computer 50 may be programmed to control a cable management system (not shown). For example, motion control application software running on computer 50 can control a cable motor 48 of the cable management system. When the blade crawler is operated, one or more cables need to accompany the crawler down the length of the airfoil-shaped body, e.g., a helicopter blade. The motion control software running on computer 50 synchronizes the movement of the cables with the movement of the blade crawler, extending or retracting the cables as appropriate. The computer system is programmed to control the cable motor 48 in dependence on crawler spanwise-position information derived from pulses generated by a crawler position encoder 146 (e.g., coupled to encoder wheel 156 seen in FIG. 2). In addition, the control computer 50 controls the crawler scan drive motor 132 in dependence on the pulses from a crawler position encoder 146.

When the crawler reaches a target spanwise position, the control computer 50 shuts off the crawler scan drive motor 132 and then starts an end effector scan drive motor 52, e.g., a drive motor which moves slider 116 along the guide rod 118 seen in FIG. 1. The computer system is programmed to control the end effector scan drive motor 52 in dependence on the end effector chordwise-position information derived from pulses generated by an end effector position encoder 148. In some embodiments, the drive motors may operate concurrently.

In cases where the end effector is a rotary tool (such as a scarfer), when the rotary tool reaches a target chordwise position, the control computer 50 shuts off the end effector scan drive motor 52 and then starts an end effector motor 54, e.g., a drive motor which drives rotation of the rotary tool. It should be appreciated that in cases where the end effector is emitting or ingesting a liquid or particles, the control computer will activate a pump. In cases where the elevational position of the plunger shaft 162 (see FIG. 4) is adjustable by operation of an actuator, such actuator may also be controlled by the computer.

Alternatively, in cases where a motion-producing device (such as a motor, solenoid, piston, etc.) is actuated to cause the crawler to grip the airfoil-shaped body, actuation of that motion-producing device may also be controlled by the control computer 50.

As part of the crawling automated scanner apparatus, the movement and alignment mechanisms perform multiple functions that enable the apparatus to operate in the NDI or maintenance modes: (1) causing the apparatus to move in a spanwise direction along the blade; (2) tracking the spanwise position of the apparatus relative to the blade; and (3) ensuring that the apparatus does not slip along the blade. More specifically, the chassis of the crawler should be capable of locomotion along the blade component; the spanwise position of the chassis along the blade component should be tracked to enable the operations of the apparatus to be properly conducted; and during operations where side and normal forces are acting on the end effector, the apparatus should maintain a constant position along the spanwise direction of the blade component.

Optionally, position encoders may be provided which output pulses representing the rotation of encoder wheels which respectively engage the trailing and leading edges of the airfoil-shaped body. These encoder pulses are transmitted to the control computer, which is programmed to monitor the respective displacements of those encoder wheels along both edges and then compensate if the crawler begins to rotate during spanwise translation.

In accordance with the embodiments described above, the control computer is provided with information concerning the spanwise and chordwise positions of the end effector. This functionality can be provided by any one of a multiplicity of known positional tracking mechanisms. In accordance with various alternative embodiments, an optical tracking system can be used to determine the spanwise and chordwise positions of the end effector. For example, U.S. Pat. No. 7,643,893 discloses a motion capture system wherein multiple motion capture cameras are set up around the object to be scanned to create a three-dimensional capture volume that captures motion for all six degrees-of-freedom of the object being tracked. Alternatively, the optical tracking mechanism may comprise a local positioning system of the type disclosed in U.S. Pat. No. 8,044,991. In accordance with yet another alternative embodiment, the end effector could be tracked using a GPS-like telemetry device mounted near the end effector.

In accordance with other embodiments, the spanwise position of the crawler can be tracked using a light-emitting diode and a photodiode mounted to the crawler chassis in a relationship similar to what is incorporated in an optical computer mouse. This positional tracker uses an image sensor to image naturally occurring texture in the airfoil surface. Images of the surface are captured in continuous succession and compared with each other, using a process known as digital image correlation, to determine how far the crawler has moved.

In accordance with a further alternative, a capacitive linear encoder can be used to track the spanwise position of the crawler. Respective printed circuit boards of a capacitive linear encoder can be mounted on the crawler chassis and on a confronting surface of the airfoil-shaped body (the latter being removable) so that the printed circuit boards are capacitively coupled. As the crawler moves, the capacitance changes in a linear fashion and in a repeating manner. Alternatively, inductive or magnetic linear encoders can be used.

While automated blade crawlers have been described with reference to particular embodiments, it will be understood by those skilled in the art that various changes may be made and equivalents may be substituted for elements thereof without departing from the scope of the teachings herein. In addition, many modifications may be made to adapt a particular situation to the teachings herein without departing from the essential scope thereof. Therefore it is intended that the claims set forth hereinafter not be limited to the disclosed embodiments.

As used in the claims, the term "computer system" should be construed broadly to encompass a system having at least one computer or processor, and which may have multiple computers or processors that communicate through a network or bus. As used in the preceding sentence, the terms "computer" and "processor" both refer to devices having a processing unit (e.g., a central processing unit) and some form of memory (i.e., computer-readable medium) for storing a program which is readable by the processing unit.

The invention claimed is:

1. A mechanism comprising:
   a plunger housing;
   a plunger shaft that is supported by and has a range of vertical motion relative to said plunger housing;
   a rocker pivotably coupled to a distal end of said plunger shaft by a revolute joint, said rocker comprising first and second arms, and first and second follower wheels pivotably coupled to respective distal ends of said first and second arms;
   an end effector holder attached to or integrally formed with said rocker for rotation therewith;
   an end effector; and
   means for coupling said end effector to said end effector holder in a manner that allows said end effector to tilt relative to said end effector holder in any direction in response to forces exerted on said end effector and then urges said end effector toward an untilted position when said forces are removed.

2. The mechanism as recited in claim 1, wherein said end effector comprises a non-destructive inspection sensor or sensor array.

3. The mechanism as recited in claim 2, wherein said non-destructive inspection sensor comprises a pitch-catch sensor, said pitch-catch sensor comprising a pair of contact feet.

4. The mechanism as recited in claim 1, further comprising means for urging said plunger shaft to move downward relative to said plunger housing.

5. The mechanism as recited in claim 1, further comprising means for urging said rocker toward a neutral position in response to said rocker adopting a non-neutral position.

6. An automated apparatus for moving said mechanism as recited in claim 1 over a surface of an airfoil-shaped body, comprising:
   a chassis adapted to travel along an airfoil-shaped body in a spanwise direction, said plunger housing being attached to and carried by said chassis;
   a first actuator for moving said chassis in said spanwise direction;
   a guide element mounted to said chassis, said guide element being disposed in a chordwise direction;
   a slider element slidably coupled to and movable along said guide element, said slider element being attached to or integrally formed with said plunger housing of said mechanism;

a second actuator for moving said slider element in said chordwise direction; and a computer system which is programmed to activate said first and second actuators at different times to produce rastering of said end effector.

7. The apparatus as recited in claim 6, further comprising a position tracking system which tracks the position of said end effector during rastering motion.

8. A mechanism comprising:

a plunger housing;

a plunger shaft that is supported by and has a range of vertical motion relative to said plunger housing;

a rocker pivotably coupled to a distal end of said plunger shaft by a revolute joint, said rocker comprising first and second arms, and first and second follower wheels pivotably coupled to respective distal ends of said first and second arms;

an end effector holder attached to or integrally formed with said rocker for rotation therewith, said end effector holder comprising a ring-shaped portion;

an end effector surrounded by said ring-shaped portion of said end effector holder; and an elastomeric gasket having an inner perimeter attached to said end effector and an outer perimeter attached to said ring-shaped portion of said end effector holder, wherein said end effector is suspended within said ring-shaped portion of said end effector holder by said elastomeric gasket.

9. The mechanism as recited in claim 8, wherein said elastomeric gasket has sufficient elasticity to allow said end effector to tilt relative to said end effector holder in any direction in response to forces exerted on said end effector and then urge said end effector toward an untilted position when said forces are removed.

10. The mechanism as recited in claim 8, wherein said end effector comprises a non-destructive inspection sensor or sensor array.

11. The mechanism as recited in claim 10, wherein said non-destructive inspection sensor comprises a pitch-catch sensor, said pitch-catch sensor comprising a pair of contact feet.

12. The mechanism as recited in claim 8, further comprising means for urging said plunger shaft to move downward relative to said plunger housing.

13. An automated apparatus for moving said mechanism as recited in claim 9 over a surface of an airfoil-shaped body, comprising:

a chassis adapted to travel along an airfoil-shaped body in a spanwise direction, said plunger housing being attached to and carried by said chassis;

a first actuator for moving said chassis in said spanwise direction;

a guide element mounted to said chassis, said guide element being disposed in a chordwise direction;

a slider element slidably coupled to and movable along said guide element, said slider element being attached to or integrally formed with said plunger housing of said mechanism;

a second actuator for moving said slider element in said chordwise direction; and a computer system which is programmed to activate said first and second actuators at different times to produce rastering of said end effector.

14. The apparatus as recited in claim 13, further comprising a position tracking system which tracks the position of said end effector during rastering motion.

15. A mechanism comprising:

a plunger housing;

a plunger shaft that is supported by and has a range of vertical motion relative to said plunger housing;

first elastomeric or mechanical spring means coupled to a distal end of said plunger shaft;

a rocker coupled to a distal end of said plunger shaft by said first elastomeric or spring means, said rocker comprising first and second arms, and first and second follower wheels pivotably coupled to respective distal ends of said first and second arms;

an end effector holder attached to or integrally formed with said rocker for movement therewith;

an end effector; and second elastomeric or mechanical spring means for coupling said end effector to said end effector holder, wherein said first elastomeric or mechanical spring means enable said rocker to tilt relative to said plunger shaft and said second elastomeric or mechanical spring means enable said end effector to tilt relative to said end effector holder.

16. The mechanism as recited in claim 15, wherein said end effector comprises a non-destructive inspection sensor or sensor array.

17. The mechanism as recited in claim 15, further comprising means for urging said plunger shaft to move downward relative to said plunger housing.

18. An automated apparatus for moving an end effector over a surface of an airfoil-shaped body, comprising:

a chassis adapted to travel along an airfoil-shaped body in a spanwise direction;

a first actuator for moving said chassis in said spanwise direction;

a guide element mounted to said chassis, said guide element being disposed in a chordwise direction;

a slider element slidably coupled to and movable along said guide element;

a second actuator for moving said slider element in said chordwise direction;

a plunger housing attached to or integrally formed with said slider element;

a plunger shaft that is supported by and has a range of vertical motion relative to said plunger housing;

a rocker pivotably coupled to a distal end of said plunger shaft by a revolute joint, said rocker comprising first and second arms, and first and second follower wheels pivotably coupled to respective distal ends of said first and second arms;

an end effector holder attached to or integrally formed with said rocker for rotation therewith;

an end effector that is tiltable relative to said end effector holder; and a computer system which is programmed to activate said first and second actuators at different times to produce rastering of said end effector.

19. The apparatus as recited in claim 18, further comprising means for coupling said end effector to said end effector holder in a manner that allows said end effector to tilt relative to said end effector holder in any direction in response to forces exerted on said end effector and then urges said end effector toward an untilted position when said forces are removed.

20. The apparatus as recited in claim 18, further comprising means for urging said plunger shaft to move downward relative to said plunger housing.

21. The apparatus as recited in claim 18, further comprising means for urging said rocker toward a neutral position in response to said rocker adopting a non-neutral position.

* * * * *